(12) United States Patent
King et al.

(10) Patent No.: US 7,541,152 B2
(45) Date of Patent: Jun. 2, 2009

(54) INTEGRATED LIGHT SOURCE FOR DIAGNOSTIC ARRAYS

(75) Inventors: David A. King, Menlo Park, CA (US); Richard J. Pittaro, San Carlos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 610 days.

(21) Appl. No.: 10/328,422

(22) Filed: Dec. 24, 2002

(65) Prior Publication Data

US 2004/0121401 A1 Jun. 24, 2004

(51) Int. Cl.
*G01N 33/53* (2006.01)
(52) U.S. Cl. ........................................ 435/7.1
(58) Field of Classification Search ................. 435/7.1, 435/4, 6, 7.2, 7.4, 7.5, 7.8, 7.9–7.95, 283.14, 435/287.1–289.1, 973, 285.2; 436/514, 517, 436/518, 523–527, 544–546; 422/55, 82.05–82.11
See application file for complete search history.

(56) References Cited

U.S. PATENT DOCUMENTS

| | | | |
|---|---|---|---|
| 5,143,854 A | 9/1992 | Pirrung et al. | |
| 5,265,792 A | 11/1993 | Harrah et al. | |
| 5,429,807 A | 7/1995 | Matson et al. | |
| 5,472,672 A | 12/1995 | Brennan | |
| 5,474,796 A | 12/1995 | Brennan | |
| 5,510,270 A | 4/1996 | Fodor et al. | |
| 5,525,466 A * | 6/1996 | Slovacek et al. | 435/6 |
| 5,552,270 A | 9/1996 | Khrapko et al. | |
| 5,633,724 A | 5/1997 | King et al. | |
| 5,812,272 A | 9/1998 | King et al. | |
| 5,851,778 A * | 12/1998 | Oh et al. | 435/7.9 |
| 6,762,025 B2 * | 7/2004 | Cubicciotti | 435/6 |
| 6,936,428 B2 * | 8/2005 | Davis et al. | 435/7.21 |
| 6,972,198 B2 * | 12/2005 | Craig et al. | 436/164 |

FOREIGN PATENT DOCUMENTS

| | | |
|---|---|---|
| EP | 0268237 B2 | 12/2002 |
| WO | WO 89/10977 | 11/1989 |
| WO | WO 92/10587 | 6/1992 |
| WO | WO 92/10588 | 6/1992 |

OTHER PUBLICATIONS

Myung et al., "Electrogenerated Chemiluminescence of CdSe nanocrystals", Nano Letters, (2002), vol. 2, No. 11, 1315-1319.*

* cited by examiner

*Primary Examiner*—Ann Y Lam

(57) ABSTRACT

The present invention relates to methods of detecting analytes in a molecular array. More specifically, the invention relates to compositions and methods of illuminating or irradiating analytes bound to a feature on an array.

21 Claims, 3 Drawing Sheets

US 7,541,152 B2

INTEGRATED LIGHT SOURCE FOR DIAGNOSTIC ARRAYS

FIELD OF THE INVENTION

The present invention relates to methods of detecting analytes in a molecular array. More specifically, the invention relates to compositions and methods of illuminating or irradiating analytes bound to a feature on an array.

BACKGROUND OF THE INVENTION

Molecular arrays have been successfully used to perform analytical assays. Such arrays may be used for detection of antibody recognition, analysis of nucleic acid molecules, peptide detection, drug screening, genetic typing and fingerprinting, and disease diagnosis.

Typically, an array contains binding molecules of several disparate species of a single type or class of molecule (e.g., DNA, or protein), each species being placed on one or more points, or features, on an array. Analytes, such as those found in a DNA sample, are usually washed over the entire array in a liquid medium. Analytes bind to specific features in the array because of specific interactions between the analytes and binding molecules. Examples of such specific interactions include, but are not limited to, antibody-antigen interactions, sequence specific nucleic acid binding, ligand-receptor interactions, and binding protein-nucleic acid interactions.

When an analyte is bound to a specific feature of an array, the presence of the analyte is typically indicated by a fluorescent molecule. The fluorescent molecule is either attached to the analyte prior to washing over the array, or it is attached afterwards. The result is that fluorescent molecules are immobilized on those features on the array where binding of an analyte has occurred.

Fluorescent molecules typically absorb light of a specific wavelength, then emit light at a second wavelength. Detection of light of this second wavelength from a feature on an array indicates the presence of the analyte.

SUMMARY OF THE INVENTION

The present invention relates to the attachment of light-emitting particles to the features of an analytical array, wherein the light emitted from the particles is sufficient to excite a second light-emitting molecule such that it emits a signal characteristic of the second light-emitting molecule.

In certain embodiments, methods of illuminating a target molecule on an analytical array are given. In certain embodiments, these methods comprise attaching a lumophore to a feature in the array, causing the lumophore to emit light sufficient to excite a fluorophore, exciting a fluorophore with the light from the first lumophore, and detecting the light from the fluorophore.

According to certain embodiments of the invention, the lumophore is a chemiluminescent molecule. According to certain embodiments, the lumophore is a bioluminescent molecule.

An analytical array is also provided in the invention. In certain embodiments, the array comprises a light-emitting substance attached to at least one feature of the array, wherein the light-emitting substance is capable of producing light of sufficient intensity and wavelength to excite a fluorescent indicator molecule.

In certain embodiments, a kit is provided. In certain embodiments of the invention, the kit comprises, an analytical array, wherein at least one feature of the array has an attached binding molecule; and at least one carrier molecule attached to a light-emitting substance. In certain embodiments, the light-emitting substance is capable of producing light of sufficient intensity and wavelength to excite a fluorescent indicator molecule. In certain embodiments, the binding molecule and carrier molecule attach to each other when brought into contact with one another.

BRIEF DESCRIPTION OF THE FIGURES

FIG. 1a depicts bioluminescent and probe molecules attached to the array substrate. FIG. 1b depicts the contacting of fluorescently labeled target molecules and a reactive substrate to the array shown in FIG. 1a. FIG. 1c depicts the transference of light between the bioluminescent molecules and the fluorescently labeled target molecules.

FIG. 2a depicts antigens and probe molecules attached to the army substrate. FIG. 2b depicts the contacting of fluorescently labeled target molecules and first-color chemiluminescent molecules to the array shown in FIG. 2a. FIG. 2c depicts the contacting of second-color chemiluminescent molecules to the array shown in FIG. 2b.

FIG. 3a depicts antigens and probe molecules attached to the array substrate. FIG. 3b depicts the contacting of a sample and antibodies comprising quantum dots to the array shown in FIG. 3a. FIG. 3c depicts the application of an electric current to the array shown in FIG. 3b.

DETAILED DESCRIPTION OF THE INVENTION

Figure 1:
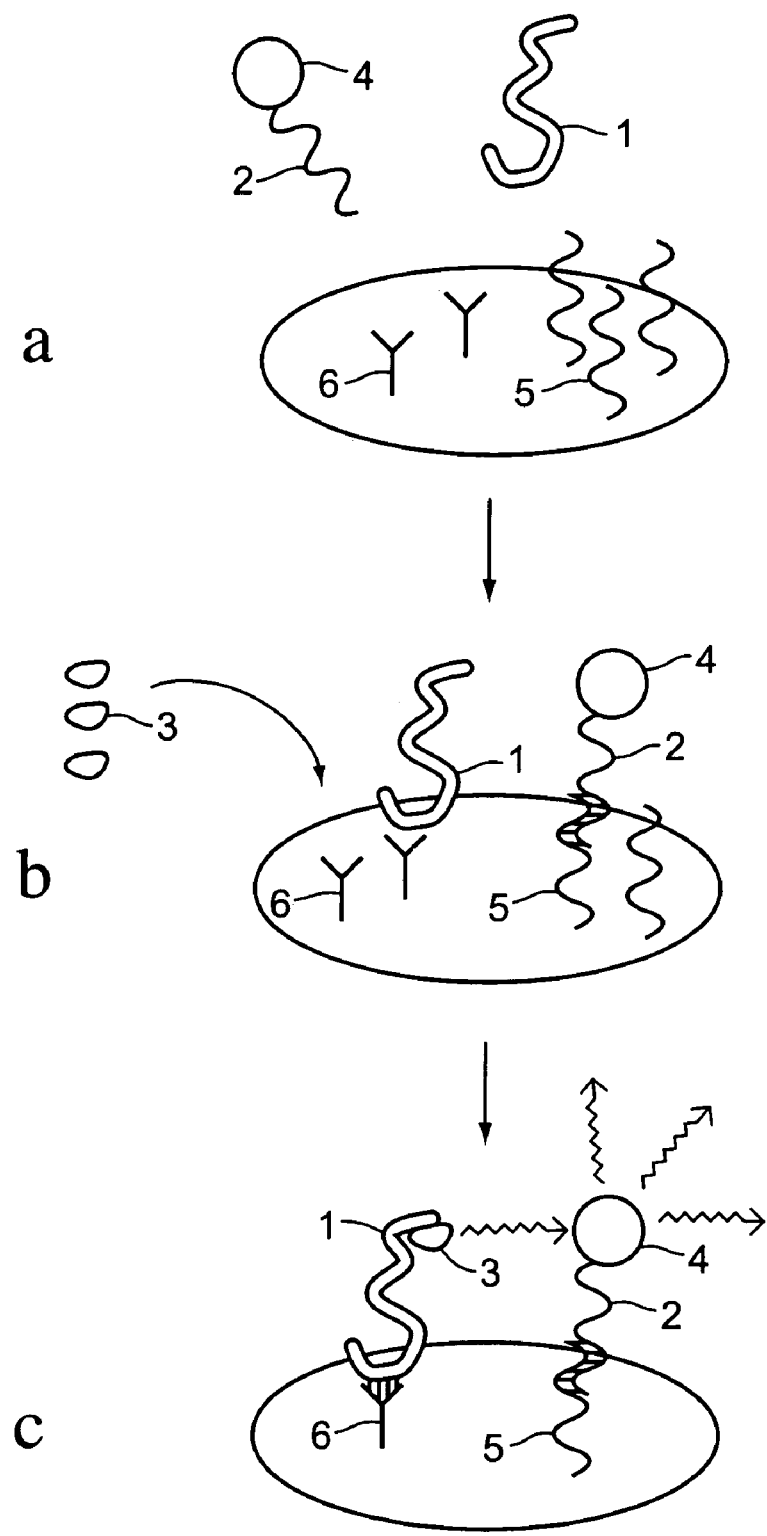
FIGS. 1a, 1b and 1c show an array comprising several features.

It is to be understood that both the foregoing general description and the following detailed description are exemplary and explanatory only and are not restrictive of the invention, as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Definitions

An "array" or "molecular array," as used herein, is an arrangement of features on a substrate or support in which each feature is located at a predetermined location relative to the other features of the array. Each feature of the array contains one or more known species of probe molecule specific for one or more targets, such that the presence of a given target molecule can be detected at a specific feature of the array.

One of skill in the art will appreciate that there are several methods of manufacturing arrays, including, but not limited to, methods described in U.S. Pat. No. 5,812,272 and PCT application PCT/US91/09217 (Publication No. WO 92/10587).

"Features" of an array are the locations, spots, pixels, or coordinates at which any given species of probe molecule or group of probe molecules is attached.

A "lumophore" or a "luminescent" molecule is any molecule capable of emitting light. These terms include, but are not limited to, enzymatic bioluminescent molecules, chemiluminescent molecules, fluorophores or fluorescent molecules that emit light in response to radiation, molecules that emit light in response to an electrical current, and quantum dots.

Chemiluminescent molecules are those molecules that, as the result of a chemical reaction, produce light. Bioluminescent molecules are those molecules that, as the result of an enzymatic reaction acting on a chemical precursor, produces a compound that produces light.

"Fluorophores" as used herein, are those molecules that fluoresce or emit light at a specific wavelength after excitation by a light of typically a different wavelength. Fluorophores include, but are not limited to, fluoresceins (see, e.g., U.S. Pat. Nos. 5,188,934; 6,008,379; and 6,020,481), rhodamines (see, e.g., U.S. Pat. Nos. 5,366,860; 5,847,162; 5,936,087; 6,051,719; and 6,191,278), benzophenoxazines (see, e.g., U.S. Pat. No. 6,140,500), energy-transfer fluorescent dyes, comprising pairs of donors and acceptors (see, e.g., U.S. Pat. Nos. 5,863,727; 5,800,996; and 5,945,526), and cyanines (see, e.g., Kubista, WO 97/45539), as well as any other fluorescent moiety capable of generating a detectable signal. Examples of fluorescein dyes include, but are not limited to, 6-carboxyfluorescein; 2',4',1,4,-tetrachlorofluorescein; and 2',4',5',7',1,4-hexachlorofluorescein. Fluorescent signals are detected by a variety of methods and apparatus, including, but not limited to U.S. Pat. No. 5,633,724.

A "fluorescent indicator molecule" refers to any molecule that fluoresces in direct of indirect response to the presence of an analyte. Thus, the presence of an analyte, in certain embodiments, can be determined by the presence of fluorescence or of the fluorescent indicator molecule.

"Quantum dots" refer to the semiconductor nanocrystalline compounds described in U.S. Pat. Nos. 5,990,479 and 6,207,392 B1, and in "Quantum-dot-tagged microbeads for multiplexed optical coding of biomolecules," Han et al., Nature Biotechnology, 19:631-635, 2001.

The terms "polynucleotide" and "oligonucleotide" mean polymers of nucleotide monomers, including analogs of such polymers, including double and single stranded deoxyribonucleotides, ribonucleotides, α-anomeric forms thereof, and the like. Descriptions of how to synthesize oligonucleotides can be found, among other places, in U.S. Pat. Nos. 4,373,071; 4,401,796; 4,415,732; 4,458,066; 4,500,707; 4,668,777; 4,973,679; 5,047,524; 5,132,418; 5,153,319; and 5,262,530. Polynucleotides and oligonucleotides can be of any length.

The term "target" according to the present invention comprises a specific nucleic acid or peptide sequence, the presence or absence or sequence of which is to be detected. The person of ordinary skill will appreciate that while a target polynucleotide is typically described as a single-stranded molecule, the opposing strand of a double-stranded molecule comprises a complementary sequence that may also be used as a target.

The term "probe" according to the present invention comprises a nucleic acid or peptide sequence that binds specifically to a target. One of ordinary skill will appreciate that a probe for a target polynucleotide is typically a nucleic acid sequence designed to complement a specific portion of the target. A probe for a target peptide may be an antibody, as a nonlimiting example.

As used herein, the term "binding molecule" refers to a molecule, placed or attached to a substrate or support, that is used to bind or attach other molecules. In certain embodiments, binding molecules are specific for the type of molecule to which they bind. As a nonlimiting example, an antibody may be used as a binding molecule to specifically bind a unique peptide.

As used herein, the term "carrier molecule" refers to a molecule that can bind or attach to a binding molecule. In certain embodiments, the carrier molecule is attached to a second molecule. The second molecule may be, for example, a lumophore or a fluorophore.

One of ordinary skill will appreciate that several methods are available for attaching probe molecules to the substrate of the array. For example, attachment methods may include covalent bonding, ionic bonding, UV crosslinking, and attachment by pairs of affinity molecules. Non-limiting examples of such pairs of affinity molecules include, but are not limited to, biotin and avidin, biotin and streptavidin, receptor and ligand, antibody and ligand, antibody and antigen, and a polynucleotide sequence and its complement. In certain embodiments, pairs of affinity molecules that are bound may be unbound. For example, a polynucleotide sequences that are hybridized may be denatured, and biotin bound to streptavidin may be heated and become unbound.

"Antibodies," as used herein, refer to either whole antibodies or antibody fragments. Antibodies may be monoclonal or polyclonal in origin. Peptides derived from nucleic acids that encode antibodies, wherein the peptides bind to antigens with some specificity, are also encompassed by this term.

Methods of Detecting Target Molecules With An Integrated Light Source

According to certain embodiments of the invention, method of generating light sufficient to excite fluorescence at a feature within an array. In certain embodiments, these methods comprise attaching a light-emitting substance to a feature. In certain embodiments, the light-emitting substance is capable of producing light of sufficient intensity and wavelength to excite a fluorescent indicator molecule. In certain embodiments, the methods further comprise causing the light-emitting substance to emit light.

One of ordinary skill will appreciate that there are many methods of attaching a light emitting molecule to the substrate of an array. Non-limiting methods of attaching luminescent molecules include covalent chemical bonding, UV crosslinking, and affinity pairing molecules.

According to certain embodiments of the invention, the light-emitting substance is a lumophore. In certain embodiments, the lumophore is a chemiluminescent molecule. In certain embodiments, the chemiluminescent molecule is selected from a group comprising AMPPD, luminol, and isoluminol.

According to certain embodiments, the lumophore is a bioluminescent molecule. In further embodiments of the invention, the bioluminescent molecule is selected from a group comprising luciferase, glucose oxidase, and glucose 6-phosphate dehydrogenase.

According to certain embodiments of the invention, the light producing substance is a substance that generates light in response to an electrical current. In certain embodiments, the substance that produces light in response to an electrical current is a quantum dot. In certain embodiments, the electrical current is conducted through ions in an aqueous solution on the feature.

Methods Employing Removable Light Sources

According to certain embodiments, methods of generating light sufficient to excite fluorescence at a feature within an array are provided. In certain embodiments, these methods comprise attaching a light-emitting substance to a carrier molecule, wherein the light-emitting substance is capable of producing light of sufficient intensity and wavelength to excite a fluorescent indicator molecule, and attaching a binding molecule to the feature. In certain embodiments, the method further comprises contacting the carrier molecule and the binding molecule such that the binding molecule and carrier molecule attach to each other; and causing the light-emitting substance to emit light.

One of ordinary skill will appreciate that there are several reversible methods of attaching luminescent molecules to an array substrate. Methods include, but are not limited to, antibody-antigen pairing, specific polynucleotide hybridization, and other affinity molecule interactions (e.g, ligand-receptor interactions, streptavidin-biotin interactions, etc.).

In certain embodiments of the invention, the binding molecule is an antibody, wherein the antibody possesses affinity for the carrier molecule. In certain embodiments of the invention, the carrier molecule is an antibody, wherein the antibody possesses affinity for the binding molecule. In certain embodiments of the invention, the carrier molecule and the binding molecule are polynucleotides, wherein the binding molecule is complementary to the carrier molecule.

In certain embodiments of the invention, the light-emitting substance is a lumophore. In certain embodiments, the lumophore is a chemiluminescent molecule. In certain embodiments, the chemiluminescent molecule is selected from a group comprising AMPPD, luminol, and isoluminol. In certain embodiments, the lumophore is a bioluminescent molecule. In certain embodiments, the bioluminescent molecule is selected from a group comprising luciferase, glucose oxidase, and glucose 6-phosphate dehydrogenase.

In certain embodiments of the invention, the light producing substance is a substance that generates light in response to an electrical current. In certain embodiments, the substance that produces light in response to an electrical current is a quantum dot. In certain embodiments, the electrical current is conducted through ions in an aqueous solution on the feature.

Arrays

An analytical array is also provided in the invention. In certain embodiments, the array comprises a light-emitting substance attached to at least one feature of the array, wherein the light-emitting substance is capable of producing light of sufficient intensity and wavelength to excite a fluorescent indicator molecule.

According to certain embodiments the light-emitting substance is a lumophore. In certain embodiments, the lumophore is a chemiluminescent molecule. In certain embodiments, the chemiluminescent molecule is selected from a group comprising AMPPD, luminol, and isoluminol.

According to certain embodiments, the lumophore is a bioluminescent molecule. In certain embodiments, the bioluminescent molecule is selected from a group comprising luciferase, glucose oxidase, and glucose 6-phosphate dehydrogenase. In certain embodiments, the light emitting substance is a quantum dot.

Kits

In certain embodiments, a kit is provided. In certain embodiments of the invention, the kit comprises, an analytical array, wherein at least one feature of the array has an attached binding molecule; and at least one carrier molecule attached to a light-emitting substance. In certain embodiments, the light-emitting substance is capable of producing light of sufficient intensity and wavelength to excite a fluorescent indicator molecule. In certain embodiments, the binding molecule and carrier molecule attach to each other when brought into contact with one another.

In certain embodiments, the binding molecule is an antibody, wherein the antibody possesses affinity for the carrier molecule. In certain embodiments, the carrier molecule is an antibody, wherein the antibody possesses affinity for the binding molecule.

In certain embodiments, the light-emitting substance is a lumophore. In certain embodiments, the lumophore is a chemiluminescent molecule. In certain embodiments, the chemiluminescent molecule is selected from a group comprising AMPPD, luminol, and isoluminol. In certain embodiments, the lumophore is a bioluminescent molecule. In certain embodiments, the bioluminescent molecule is selected from a group comprising luciferase, glucose oxidase, and glucose 6-phosphate dehydrogenase.

According to certain embodiments, the light producing substance is a substance that generates light in response to an electrical current. In certain embodiments, the substance that produces light in response to an electrical current is a quantum dot. In certain embodiments, the electrical current is conducted through ions in an aqueous solution on the feature.

EXEMPLARY EMBODIMENTS

The examples described herein are for illustrative purposes, and do not limit the scope of the invention in any way.

Example 1

An array may be comprised of several features that have bioluminescent enzymes, such as luciferase molecules, attached at the features to the array substrate. See FIG. 1a. The attachment of the enzyme (1) may be through an antibody (6), acting as a binding molecule, to the enzyme attached to the substrate, or by UV crosslinking.

When a sample containing fluorescently labeled target molecules (2) is placed on the array, a reactive substrate (3), such as luciferin, is included in the aqueous media with the sample. See FIG. 1b. The enzyme (1), acting on the substrate (3), produces light. The light, of a sufficient intensity to induce fluorescence, is absorbed by the fluorescent molecules attached to targets (2) bound to the probe molecules (5). FIG. 1c. The light emitted from the fluorescent molecules is of a different wavelength than that emitted by the bioluminescent molecules.

When a target (2) is bound to a feature of the array, the wavelength of the fluorescent label is detected at that feature.

Example 2

Features of an array possess antigen molecules (7) at each of the features of the array. Chemiluminescent molecules (8) of different wavelengths are covalently attached to antibodies (9) acting as carrier molecules. The antibodies (9) are designed to be specific for the antigens (7), acting as binding molecules, attached to the array, and not crossreactive to the other molecules. See FIG. 2a.

Different target molecules (2) are labeled with different fluorophores (4) that are excited by different wavelengths. After a sample is placed on the array and target molecules (2) are bound to the features, antibodies possessing a first color chemiluminescent molecule (8a) are placed on the array. The first chemiluminescent molecules (8a), attached to the antibodies, are exposed to a catalyst which causes them to emit light of a first color. See FIG. 2b.

The first color excites a first fluorescent molecule (4a) attached to some of the target molecules. These target molecules (2) are then detected at the features to which they are bound.

Figure 2:
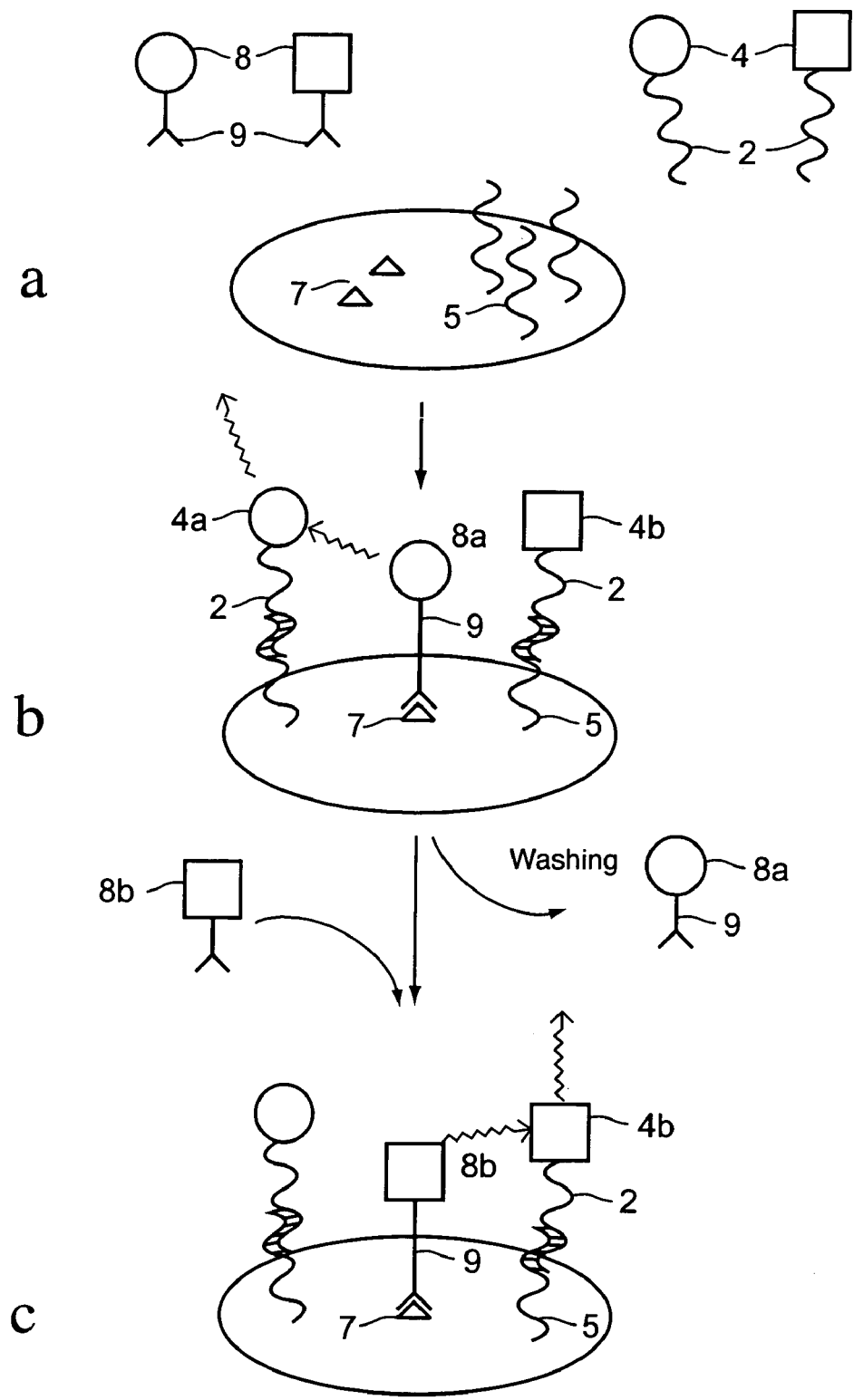
FIGS. 2a, 2b and 2c show an array comprising several features.

After detection, the antibodies are released from the antigens, and washed off of the array substrate. See FIGS. 2b and 2c. Another antibody possessing a second color chemiluminescent molecule (8b) is placed on the array. FIG. 2c. The second antibody is also exposed to a catalyst that causes the chemiluminescent molecules to emit a second wavelength of light. The second wavelength of light causes a second color fluorescent molecule to fluoresce. The second fluorescent signal is then detected at the features to which the concomitant target molecules are bound.

Example 3

An array is designed such that two electrodes (10 and 11) are present at each feature of an array. Electrodes at each feature are capable of conducting a electric current through a conductive aqueous medium (12) containing an appropriate concentration of salts. Antigens (7) are also attached to each feature of the array as binding molecules. See FIG. 3a.

Figure 3:
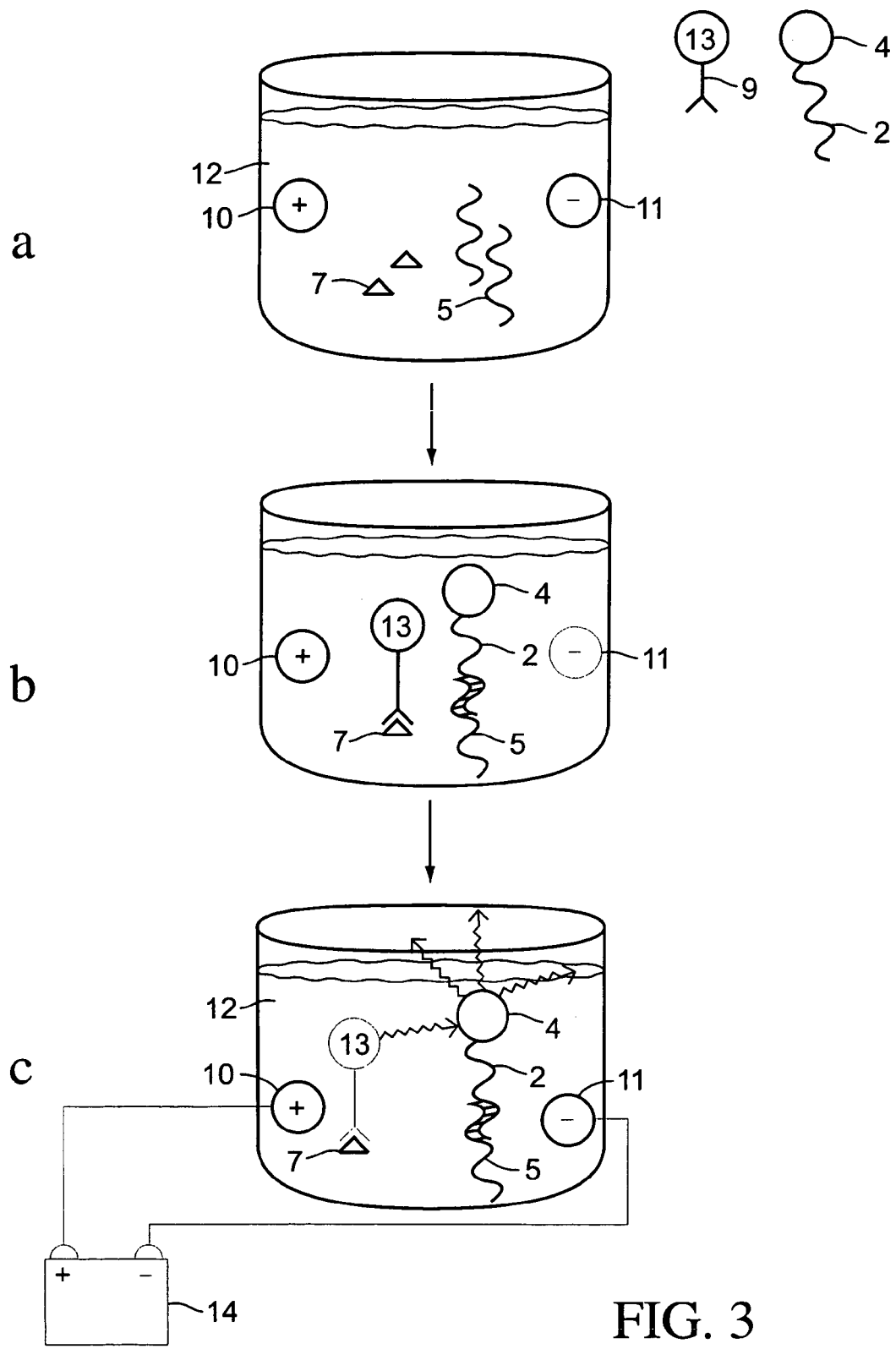
FIGS. 3a, 3b and 3c show an array comprising at least one feature, wherein there are two electrodes present at each feature.

Antibodies (9) as carrier molecules may be covalently attached to quantum dots (Cd nanocrystals) (13). After a sample is placed on an array, and target molecules (2) are bound to probes (5) on each feature, antibodies (9) are placed on the array. FIG. 3b.

An electrical current from an electrical source (14) is sent through an aqueous medium (12) at each feature by the electrodes present at each feature. See FIG. 3c. When a quantum dot (13) is exposed to an electrical current, it emits a light of a wavelength in relation to the size of the quantum dot. The light from the quantum dot (13) can excite a fluorophore (4) attached to a target molecule (2) at the feature.

What is claimed is:

1. A method of generating light sufficient to excite fluorescence from a fluorescent indicator molecule directly attached to a target molecule bound to a probe molecule at a feature within an array, comprising:
   providing an array comprising a binding molecule and a probe molecule at a feature within an array;
   contacting a target molecule having a fluorescent indicator molecule directly attached thereto to said probe molecule such that said target molecule and said probe molecule are bound to each other at said feature;
   contacting a carrier molecule to said binding molecule such that said carrier molecule and said binding molecule are attached to each other at said feature;
   contacting a light-emitting substance to said carrier molecule, wherein the light-emitting substance is capable of producing light of sufficient intensity and wavelength to excite said fluorescent indicator molecule;
   causing the light-emitting substance to emit light, wherein said light emitted from said light-emitting substance is absorbed by said fluorescent indicator molecule thereby causing said fluorescent indicator molecule to emit light; and
   detecting said light emitted from said fluorescent indicator molecule directly attached to said target molecule.

2. The method of claim 1, wherein the binding molecule is an antibody, wherein the antibody possesses affinity for the carrier molecule.

3. The method of claim 1, wherein the carrier molecule is an antibody, wherein the antibody possesses affinity for the binding molecule.

4. The method of claim 1, wherein the carrier molecule and the binding molecule are polynucleotides, wherein the binding molecule is complementary to the carrier molecule.

5. The method of claim 1, wherein the light-emitting substance is a lumophore.

6. The method of claim 5, wherein the lumophore is a chemiluminescent molecule.

7. The method of claim 6, wherein the chemiluminescent molecule is selected from a group comprising AMPPD, luminol, and isoluminol.

8. The method of claim 5, wherein the lumophore is a bioluminescent molecule.

9. The method of claim 8, wherein the bioluminescent molecule is selected from a group comprising luciferase, glucose oxidase, and glucose 6-phosphate dehydrogenase.

10. The method of claim 1, wherein the light-emitting substance is a substance that generates light in response to an electrical current.

11. The method of claim 10, wherein the substance that produces light in response to an electrical current is a quantum dot.

12. The method of claim 10, wherein the electrical current is conducted through ions in an aqueous solution on the feature.

13. A method of generating light sufficient to excite
   fluorescence from a fluorescent indicator molecule directly attached to a target molecule bound to a probe molecule at a feature within an array, comprising:
   contacting a light-emitting substance to said feature, wherein the light emitting substance: a) binds to a binding molecule that is present within said feature in addition to said probe molecule and b) is capable of producing light of sufficient intensity and wavelength to excite said fluorescent indicator molecule;
   causing the light-emitting substance to emit light, wherein said light emitted from said light-emitting substance is absorbed by said fluorescent indicator molecule thereby causing said fluorescent indicator molecule to emit light; and
   detecting said light emitted from said fluorescent indicator molecule directly attached to said target molecule, wherein said target molecule is bound to said probe molecule at said feature.

14. The method of claim 13, wherein the light-emitting substance is a lumophore.

15. The method of claim 14, wherein the lumophore is a chemiluminescent molecule.

16. The method of claim 15, wherein the chemiluminescent molecule is selected from a group comprising AMPPD, luminol, and isoluminol.

17. The method of claim 14, wherein the lumophore is a bioluminescent molecule.

18. The method of claim 17, wherein the bioluminescent molecule is selected from a group comprising luciferase, glucose oxidase, and glucose 6-phosphate dehydrogenase.

19. The method of claim 13, wherein the light-emiting substance is a substance that generates light in response to an electrical current.

20. The method of claim 19, wherein the substance that produces light in response to an electrical current is a quantum dot.

21. The method of claim 19, wherein the electrical current is conducted through ions in an aqueous solution on the feature.

* * * * *